(12) United States Patent
Olek et al.

(10) Patent No.: US 11,667,973 B2
(45) Date of Patent: Jun. 6, 2023

(54) ENDOSIALIN (CD248) AS EPIGENETIC MARKER FOR THE IDENTIFICATION OF IMMUNE CELLS, IN PARTICULAR NAÏVE CD8+ T-CELLS

(71) Applicant: Precision for Medicine GmbH, Berlin (DE)

(72) Inventors: Sven Olek, Berlin (DE); Janika Josephin Schulze, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 29 days.

(21) Appl. No.: 16/758,896

(22) PCT Filed: Oct. 25, 2018

(86) PCT No.: PCT/EP2018/079290
§ 371 (c)(1),
(2) Date: Apr. 24, 2020

(87) PCT Pub. No.: WO2019/081642
PCT Pub. Date: May 2, 2019

(65) Prior Publication Data
US 2020/0370117 A1    Nov. 26, 2020

(30) Foreign Application Priority Data
Oct. 26, 2017   (DE) .......................... 102017125150.2

(51) Int. Cl.
*C12Q 1/6881*   (2018.01)

(52) U.S. Cl.
CPC ..... *C12Q 1/6881* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 2011/0117551 A1* | 5/2011 | Van Criekinge | C12Q 1/6886 435/6.11 |
| 2012/0034228 A1* | 2/2012 | Kufer | A61P 19/00 435/254.2 |
| 2014/0227703 A1* | 8/2014 | Olek | C12Q 1/6881 435/6.11 |

FOREIGN PATENT DOCUMENTS

| | | |
|---|---|---|
| WO | WO 98/10284 A1 | 3/1998 |
| WO | WO 2006/060719 A2 | 6/2006 |
| WO | WO 2012/162660 A2 | 11/2012 |
| WO | WO 2013/14122 A1 | 1/2013 |
| WO | WO 2014/080017 A1 | 5/2014 |
| WO | WO2014080017 A1 * | 5/2014 ............... C12Q 1/68 |
| WO | WO 2014/170497 A2 | 10/2014 |
| WO | WO 2017/050925 A1 | 3/2017 |

OTHER PUBLICATIONS

Antequera and Bird, Number of CpG Islands and Genes in Human and Mouse, Proc Natl Academy of Science USA 90: 11995-9, 1993.
Booth, Michael J. et al., Quantitative Sequencing of 5-Methylcytosine and 5-Hydroxymethylcytosine at Single-Base Resolution, Science May 18, 2012, vol. 336, No. 6083, pp. 934-937.
Esteller, M., CpG Island Hypermethylation and tumor Suppressor Genes: a Booming Present, a Brighter Future, Oncogene 21:5427-5440, 2002.
Facciponte, J. et al., Tumor endothelial marker 1-specific DNA vaccination targets tumor vasulature, Journal of Clinical Investigation, vol. 124, No. 4, Mar. 18, 2014, 1497-1511.
Hardie, D.L. et al., The stromal cell antigen CD248 (endosialin) is expresssed on naive CD8+ human T Calls and regulates proliferation: CD248 on naïve CD8 T cells, Immunology, vol. 133, No. 3, Apr. 6, 2011.
Jones and Laird, Cancer-Epigenetics Comes of Age, Nature Genetics 21: 163-167, 1999.
Kristensen and Hansen, PCR-Based Methods for Detecting Single-Locus DNA Methylation Biomarkers in Cancer Diagnostics, Prognostics, and Response to Treatment, Clinical Chemistry 55:8 1471-1483 (2009).
Laird, Peter W., The Power and The Promise of DNA Methylation Markers, Nature Reviews Cancer 3, pp. 253-266 (2003).
Liina Tserel et al., Age-related profiling of DNA methylation in CD8+ T cells reveals changes in immune response and transcriptional regulator genes, Scientific Reports, vol. 5, No. 1, Aug. 19, 2015.
Suarez-Alvarez et al, Phenotypic characteristics of aged CD4+ CD28null T lymphocytes are determined by changes in the whole-Genome DNA methylation pattern, Aging Cell, Apr. 2017, 16(2): 293-303, Epub Dec. 27, 2016.

* cited by examiner

*Primary Examiner* — Amanda Haney
(74) *Attorney, Agent, or Firm* — BakerHostetler (57) ABSTRACT

The present invention relates to a method, in particular an in vitro method, for identifying specific immune cells, in particular naïve CD8+ T-cells, comprising analyzing the methylation status of at least one CpG position in the mammalian gene region for endosialin (CD248), wherein a demethylation or lack of methylation of said gene region is indicative for a naïve CD8+ T-cell, when compared to a non-naïve CD8+ T-cell or any other (blood) cell type. The analyses according to the invention can identify naïve CD8+ T-cells on an epigenetic level and distinguish them from all other cells in complex samples, such as, for example, other blood or immune cells. The present invention furthermore provides an improved method for quantifying naïve CD8+ T-cells, in particular in com naïve CD8+ T-cells complex samples. The method can be performed with or without a step of purifying and/or enriching cells, preferably in whole blood and/or non-trypsinized tissue.

15 Claims, 1 Drawing Sheet
Specification includes a Sequence Listing.

ENDOSIALIN (CD248) AS EPIGENETIC MARKER FOR THE IDENTIFICATION OF IMMUNE CELLS, IN PARTICULAR NAÏVE CD8+ T-CELLS

CROSS-REFERENCE TO RELATED APPLICATIONS

This application is a 35 U.S.C. § 371 national phase application of International Patent Application No. PCT/EP2018/079290, filed Oct. 25, 2018, which claims priority to German Patent Application No. 102017125150.2, filed Oct. 26, 2017, the entire disclosures of each of which are incorporated herein by reference in their entirety.

The Sequence Listing for this application is labeled "113828.000021_Sequence Listing.txt", which was created on Apr. 22, 2020 and is 4 Kilobytes. The entire content is incorporated herein by reference in its entirety.

The present invention relates to a method, in particular an in vitro method, for identifying specific immune cells, in particular naïve CD8+ T-cells, comprising analyzing the modification, such as the methylation status, of at least one CpG position in the mammalian gene region for endosialin (CD248), wherein a demethylation or lack of modification such as methylation, of said gene region is indicative for a naïve CD8+ T-cell, when compared to a non-naïve CD8+ T-cell or any other (blood) cell type. The analyses according to the invention can identify naïve CD8+ T-cells on an epigenetic level and distinguish them from all other cells in complex samples, such as, for example, other blood or immune cells. The present invention furthermore provides an improved method for quantifying naïve CD8+ T-cells, in particular in com naïve CD8+ T-cells complex samples. The method can be performed with or without a step of purifying and/or enriching cells, preferably in whole blood and/or non-trypsinized tissue.

Furthermore, the present invention relates to a kit for performing the above methods as well as respective uses thereof It is one aim of this invention to provide a novel, more robust means to quantitatively detect and measure naïve CD8+ T-cells within any body fluid, such as blood, any solid organ or tissue or of a mammal.

BACKGROUND OF THE INVENTION

Naïve CD8+ T-cells are T-cells that have differentiated in bone marrow, and successfully undergo the positive and negative processes of central selection in the thymus, and constitute the naïve form of cytotoxic T cells (CD8+). A naïve T cell is considered mature and, unlike activated or memory T cells, has not encountered its cognate antigen within the periphery. Naïve T cells are commonly characterized by the surface expression of L-selectin (CD62L); the absence of the activation markers CD25, CD44 or CD69; and the absence of memory CD45RO isoform. They are also described as expressing functional IL-7 receptors, consisting of subunits IL-7 receptor-$\alpha$, CD127, and common-$\gamma$chain, CD132.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics - heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

The isolation of naive CD8$^+$ T cells can be performed in a two-step procedure. First, naive T cells are enriched by depletion of non-naive T cells and NK cells, which are indirectly magnetically labeled with a cocktail of biotin-conjugated antibodies and Anti-Biotin MicroBeads. In a second step, the enriched naive T cells are labeled with CD8 MicroBeads for subsequent positive selection of the CD8$^+$ naive T cells.

WO 98/10284 describes methods to capture, purify and expand antigen-specific T lymphocytes. WO 2006/060719 discloses methods of detecting and isolating endosialin-positive cells using antibodies, derivatives and fragments.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

WO 2013/014122 relates to a method, in particular an in vitro method for identifying natural killer cells and their subgroups in a mammal, preferably CD3 negative, non T-lymphocyte derived NK cells, which often express the surface proteins CD56 and/or CD 16, comprising analyzing the accessibility of the genomic DNA for OSBPL, such as OSBPL5, to bisulfite conversion and/or the methylation status of at least one CpG position in the genes for OSBPL, such as OSBPL5.

Suarez-Alvarez et al. (Phenotypic characteristics of aged CD4+ CD28null T lymphocytes are determined by changes in the whole-genome DNA methylation pattern. Aging Cell. 2017 April;16(2):293-303. Epub 2016 Dec. 27) analyze whole-genome DNA methylation and gene expression profiles of CD28null T cells and its CD28+ counterpart. A comparative analysis revealed that 296 genes are differentially methylated between the two cell subsets. Hardie D. L. et al. (in: The stromal cell antigen CD248 (endosialin) is expressed on naive CD8+ human T cells and regulates proliferation. Immunology 133, 288-295 (2011)) disclose that CD248 is uniquely expressed by human, but not mouse (C57BL/6), $CD8^+$ naive T cells. Their data demonstrate opposing functions for CD248 on haematopoietic ($CD8^+$) versus stromal cells and suggests that CD248 helps to maintain naive $CD8^+$ human T cells in a quiescent state.

Tserel et al. (in: Tserel L, Kolde R, Limbach M, et al. Age-related profiling of DNA methylation in CD8+ T cells reveals changes in immune response and transcriptional regulator genes. *Scientific Reports*. 2015;5:13107) disclose age-related changes in DNA methylation and gene expression in CD4+ and CD8+ T cells from younger and older individuals. They observed marked difference between T cell subsets, with increased number of methylation changes and higher methylome variation in CD8+ T cells with age. The majority of age-related hypermethylated sites were located at CpG islands of silent genes and enriched for repressive histone marks. Specifically, in CD8+ T cell subset they identified strong inverse correlation between methylation and expression levels in genes associated with T cell mediated immune response (LGALS I, IFNG, CCL5, GZMH, CCR7, CD27 and CD248) and differentiation (SATB1, TCF7, BCL11B and RUNX3). Their results thus suggest a link between age-related epigenetic changes and impaired T cell function. Older individuals showed increased methylation and decreased expression of CD248, but also vaccine response problems.

In view of the above, it is an object of the present invention to provide an improved and in particular robust method based on DNA-methylation analysis as a superior tool in order to more conveniently and reliably detect, identify, discriminate, and quantify specific immune cells, in particular naïve CD8+ T-cells.

The present invention solves the above object by providing a method for identifying naïve CD8+ T cells in a sample derived from a human, comprising analyzing the modification, preferably methylation status, of at least one CpG position in the human gene region for endosialin (CD248), wherein preferably said gene region as analyzed is positioned according to SEQ ID No. 1, wherein a demethylation or lack of modification, preferably methylation, of said gene region is indicative for a naïve CD8+ T cell, when compared to a non-naïve CD8+ T cell.

The gene for human CD248 is found on Ensembl-ID: ENSG00000174807.

In the context of the present invention, a "gene" or "gene region" shall comprise all of the genomic regions relating to and encoding for CD248. Thus, included are enhancer regions, promoter region(s), introns, exons, and non-coding regions (5'- and/or 3'-regions) that belong to CD248. Preferred is thus a method according to the present invention, wherein the at least one CpG position is present in the 5' region upstream from the transcription start, promoter region, the 5' or 3' untranslated regions, exon, intron, exon/intron border and/or in the 3' region downstream of the transcriptional stop of the gene as analyzed.

The present invention is further based on the surprising identification of a region of the CD248 gene by the inventors, as specific epigenetic marker, allowing the identification of naïve CD8+ T cells as well as the clinical routine application of said analysis.

In the context of the present invention, the genomic region of CD248, in particular according to SEQ ID No. 1 allows the identification of naïve CD8+ T cells. Surprisingly, the discriminatory pattern of bisulfite convertible and non-convertible cytosine is particularly and even exclusively limited to the genomic region according to SEQ ID No. 1 naïve CD8+ T cells as shown using the amplicon according to SEQ ID No. 1, and in particular in the bisulfite converted sequences according to SEQ ID No. 2 or 3.

The inventors could demonstrate that in the naïve CD8+ T cells the CpG motifs as disclosed are almost completely demethylated (i.e. to more than 70%, preferably 80%, preferably, more than 90% and most preferred more than 95%), whereas the same motifs are completely methylated in all other immune cells.

The differential methylation of the CpG motifs within the aforementioned regions is a valuable tool to identify naïve CD8+ T cells, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of naïve CD8+ T cells without purification or any staining procedures.

Another preferred aspect of the method according to the present invention then further comprises a quantification of the relative amount of naïve CD8+ T cells based on comparing relative amounts of said methylation frequency in the region as analyzed with relative amounts of the methylation frequency in a control gene, such as, for example, GAPDH. Said quantification is thus achieved based on the ratio of the bisulfite convertible DNA to non-convertible DNA in the genetic region of CD248 (e.g. of SEQ ID No. 1) as described and analyzed herein. Most preferred is a quantification of the relative amount of naïve CD8+ T cells is based on an (preferably parallel or simultaneous) analysis of the relative amount of bisulfite convertible DNA of cell-specific region for CD248, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID No. 1, preferably oligomers according to any of SEQ ID No. 4 to 14.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the CD248 gene region is produced that is a particularly preferred "tool" for performing the method(s) according to the present invention. Consequently, oligomers according to any of SEQ ID No. 4 to 14 or an amplicon as amplified by a primer pair based on SEQ ID No. 4 and 5, 6 and 7, 9 and 10, and 12 and 13 as mentioned herein constitute preferred embodiments of the present invention. Thus, the sequences of SEQ ID No. 1 to 3 (and, if needed, the complementary sequences thereto) can be used to design primers for amplifications, i.e. serve as "beacons" in the sequence as relevant. Similarly, additional primers and probes can be designed based on the amplicon according to SEQ ID No. 1. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID No. 1, and is preferably selected from CpG positions 1, 2, 3, 4, 5, 6, 7, 8, 9, 10, 11, 12, 13, 14, 15, 16, 17, 18, 19, and 20 in the amplicon No. 1817 according to SEQ ID No. 1. The positions are numerically counted from the 5'-end of an amplicon as generated and analyzed, and are designated as AMP1871:118, 133, 145, 175, 207, 212, 224, 231, 243, 274, 292, 296, 319, 327, 331, 345, 363, 373, 400, 406, and 415 in FIG. 1. Preferred are combinations of 3, 4, 5, 6, 7, 8, 9, or 10 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position CpG1 to CpG 20 in the amplicon No. 1817 of the CD248 specific bisulfite convertible region (SEQ ID No. 1), or all sites as present on the bisulfite convertible region according to SEQ ID No 1. One or more of positions 118, 133, 363, 373, 400, 406, and/or 415 may be excluded.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said naïve CD8+ T cells from all major peripheral blood cell types and/or non-blood cells, preferably, but not limited to, from CD56+ NK cells, follicular helper T cells, cytotoxic T-cells, granulocytes, monocytes, B-cells, CD56++("bright") NK cells, T-helper cells, and NKT cells, and other cell types derived from other organs than blood.

In yet another preferred embodiment of the method according to the present invention, the sample is selected from a human body fluid, including human blood samples, or a tissue, organ or a sample of leukocytes or a purified or separated fraction of such tissue, organ or leukocytes or a cell type sample. The samples can be suitably pooled, if required.

Another preferred aspect of the method according to the present invention then further comprises the step of concluding on the immune status of said human based on said naïve CD8+ T cells. The naïve CD8+ T cells can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to Trypanosoma cruzi-infection, Malaria and HIV infection; Hematologic Malignancies as but not limited to chronic Myelogenous Leukemia, Multiple Myeloma, Non-Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of naïve CD8+ T cells in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said naïve CD8+ T cells as e.g. a sample for cell transfer into a patient.

Another preferred aspect of the method according to the present invention then relates to a method as above, further comprising formulating said naïve CD8+ T cells as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID No. 4 to 14, or an amplicon according to SEQ ID No. 1 to 3.

Yet another preferred aspect of the present invention then relates to a kit for identifying, quantifying, and/or monitoring naïve CD8+ T cells in a human based on the analysis of the bisulfite accessibility of CpG positions in the gene region of CD248, comprising components for performing a method according to any of claims 1 to 12, in particular a kit comprising a) a bisulfite reagent, and b) materials for the analysis of the methylation status of CpG positions selected from the CpG positions in the region according to SEQ ID NO: 1, such as an oligomer selected from the sequences according to SEQ ID NOs: 4 to 14.

The present invention also encompasses the use of oligomers or amplicon or a kit according to the present invention for identifying and/or for monitoring naïve CD8+ T cells in a human as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=$a/b$ $a=\Sigma$ (C and/or mC and/or hmC and/or fC and/or cC)
$b=\Sigma$ (C and/or mC and/or hmC and/or fC and/or cC), whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the CD248 genetic region and in particular the amplicon as described herein as a marker, the inventors very specifically identified, quantified and particularly differentiated naïve CD8+ T cells, and in their relation to other cell types in a sample, for example to other blood cells.

The invention will now be further described based on the following examples and with reference to the accompanying figures and the sequence listing, without being limited thereto. For the purposes of the present invention, all references as cited herein are incorporated by reference in their entireties.

Table No. 2 shows specificity of the TpG-specific PCR-system using test-templates i.e., mixtures of TpG- and CpG-specific plasmid-DNA.

SEQ ID No. 1 shows the genomic sequence of amplicon AMP1817 according to the present invention.

SEQ ID Nos. 2 and 3 show examples of bisulfite converted sequences of SEQ ID NO: 1.

SEQ ID Nos. 4 to 14 show the sequences of specific oligomers (primers and probes) according to the present invention. FAM =fluorescein amidite; BHQ1 =Black Hole Quencher.

EXAMPLES

Example 1

In order to identify naïve CD8+ T-cells, qPCR was performed on bisulphite converted samples stemming from the human genomic region according to the following sequence (AMP1817, SEQ ID No. 1), relevant CpGs are indicated in bold:

CATCTTCCTCATCCTCCCCGTCATCCAGCAACTCATCTCGAGGTCCTG
GGAAGCCTGGGCACCCATGGCCCCTGCAGGGCTGCAGCTGATGCCATCA
GCCTCCAGCTCATGTCCCTCGCTACAATAACACTCGAAGCCACCAACGT
AGTTGACACACATCTGCTGGCACACACCGGCAATCTGGCACTCATCTGT
GTCCACACAGCCGGTGCGGATCATCCTCCGCTGGCCGGAAACCCAGGCGA
CAGTGGCAGCTGTAGCCTTGTGGCCCACCGGGCTCACACTGCTGCTCGC
ACCGGAGCCTGGGCACAGGGGTCCTCGCAACTGCGCCCGTCTGCTGCCAG
CCCGGAAGCCCTCAGTGCAGCGGCAGGACACGTGACCATCCACCTCCTCC
ACACATTCGTGTTCGCAGCCCCCGTTGTCAGGGCTGCAGCCAGTCCC

The following sequences show examples of bisulfite converted sequences of SEQ ID NO: 1:

BIF
(SEQ ID NO: 2):
TATTTTTTTATTTTTTTGTTATTTAGTAATTTATTTTTGAGGTTTTGG
GAAGTTTGGGTATTTATGGTTTTTGTAGGGTTGTAGTTGATGTTATTAGT
TTTTAGTTTATGTTTTTTGTTATAATAATATTTGAAGTTATTAATGTAGT
TGATATATATTTGTTGGTATATATTGGTAATTTGGTATTTATTTGTGTTT
ATATAGTGGTGTGGATTATTTTTGTTGGTTGGAAATTTAGGTGATAGTG
GTAGTTGTAGTTTTGTGGTTTATTGGGTTTATATTGTTGTTTGTATGGAG
TTTGGGTATAGGGGTTTTTGTAATTGTGTTTGTTTGTTGTTAGTTGGAAG
TTTTTAGTGTAGTGGTAGGATATGTGATTATTTATTTTTTTTTATATATTT
GTGTTTGTAGTTTTTGTTGTTAGGGTTGTAGTTAGTTTT

B2F
(SEQ ID NO: 3):
CATCTTCCTCATCCTCCCCGTCATCCAACAACTCATCTCCGAAATCCTAA
AAAACCTAAACACCCATAACCCCTACAAAACTACAACTAATACCATCAAC
CTCCAACTCATATCCCTCGCTACAATAACACTCGAAACCACCAACGTAAT
TAACACACATCTACTAACACACACCGACAATCTAACACTCATCTATATCC
ACACAACGATACGAATCATCCTCCGCTAACCGAAAACCCAAACGACAATA
ACAACTATAACCTTATAACCCACCGAACTCACACTACTACTCGCACGAAA
CCTAAACACAAAAATCCTCGCAACTACGCCCGTCTACTACCAACCGAAAA
CCCTCAATACAACGACAAAACACGTAACCATCCACCTCCTCCACACATTC
GTATTCGCAACCCCCGTTATCAAAACTACAACCAATCCC

Figure 1:
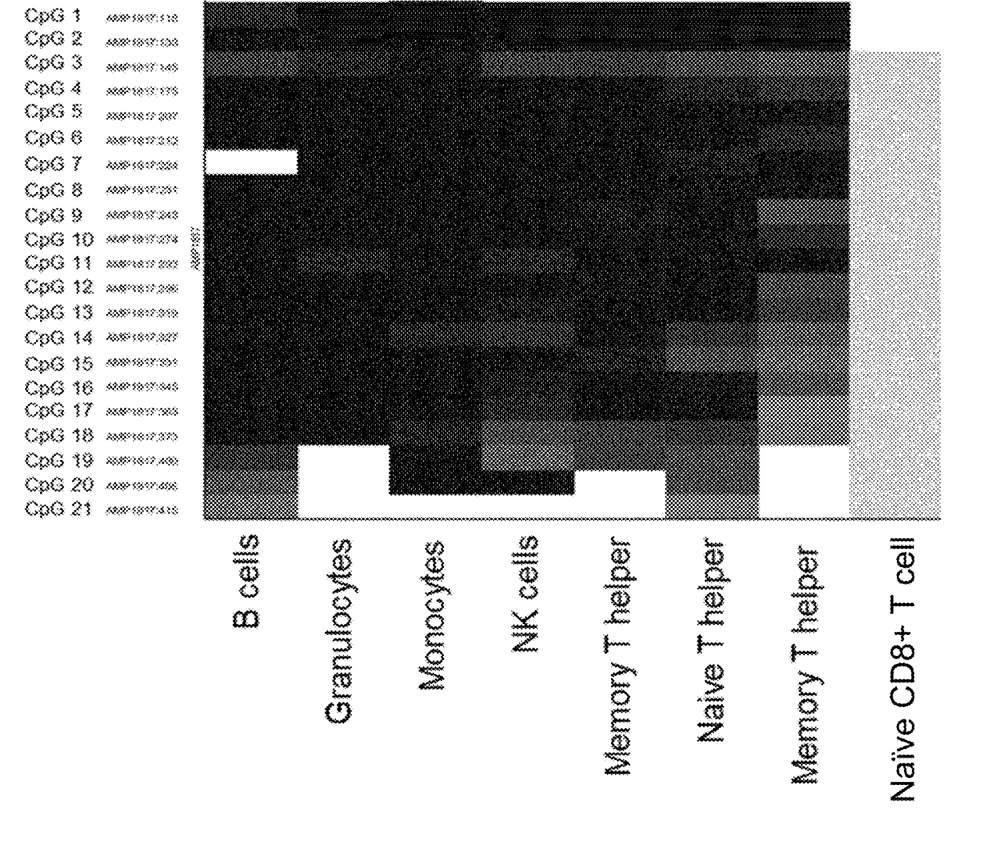
FIG. 1 shows the analysis of CpG sites on amplicon No. 1817 (SEQ ID No. 1) according to the invention. The horizontal boxes in the table correspond to the CpG positions in the amplicon as analyzed (e.g. CpG 1, 2, etc.) with the positions indicated (118, 133, 145, 175, 207, 212, 224, 231, 243, 274, 292, 296, 319, 327, 331, 345, 363, 373, 400, 406, and 415, corresponding to CpG 1, 2, 3, 4, . . . etc.), and the columns correspond to the cell types as analyzed.

For the actual epigenetic profiling of the amplicon region in blood cell subtypes, the immune cell populations as analyzed were as follows (see FIG. 1)

CTL01=CD8$^+$ cytotoxic T-cells
BLC25=B-lymphocytes
GRC52=granulocytes
MOC26=CD14$^+$ monocytes
NKC=CD56$^+$ NK-cells
NKT=CD56$^+$ CD3$^+$ NKT-cells
THC14=CD4$^+$ Helper T-cells The following table 1 shows primers and probes that were used for the qPCR (TpG Variant; demethyl-specific; CpG Variant; methyl-specific):

| | | | | | |
|---|---|---|---|---|---|
| Forward amplification primer | | | 1817-fwd | CATCTTCCTCATCCTCCC (SEQ ID No. 4) | |
| Reverse amplification primer | | | 1817-rev | GGGATTGGTTGTAGTTTTGATA (SEQ ID No. 5) | |
| Naïve CD 8 | qPCR16 | AMP1817 | qPCR16_Fw_C | CTATATCCACACAACGATACGA (SEQ ID NO: 6) | |
| | | | qPCR16_Rv_C | GTTTTCGGTTGGTAGTAGAC (SEQ ID NO: 7) | |
| | | | qPCR16_P_C | AATCCTCGCAACTACGCCCGT (SEQ ID NO: 8) | 5'FAM/ 3'BHQ1 |
| | | | qPCR16_Fw_T | TATATAGTGGTGTGGATTATTTTTT (SEQ ID NO: 9) | |
| | | | qPCR16_Rv_T | TAACAACAAACAAACACAATTACA (SEQ ID NO: 10) | |
| | | | qPCR16_P_T | CAAACTCCATACAAACAACAA TATAAACCCAA (SEQ ID NO: 11) | 5'FAM/ 3'BHQ1 |
| Naïve CD 8 | qPCR16-2 | AMP1817 | qPCR16_Fw_C | CTATATCCACACAACGATACGA (SEQ ID NO: 6) | |
| | | | qPCR16_Rv_C | GTTTTCGGTTGGTAGTAGAC (SEQ ID NO: 7) | |

|  |  |  |
|---|---|---|
| qPCR16_P_C | AATCCTCGCAACTACGCCCGT (SEQ ID NO: 8) | 5'FAM/ 3'BHQ1 |
| qPCR16-2_Fw_T | GTGTTTATATAGTGGTGTGGATTATTTTTT (SEQ ID NO: 12) |  |
| qPCR16-2_Rv_T | CTAACAACAAACAAACACAATTACA (SEQ ID NO: 13) |  |
| qPCR16_P_T | CAAACTCCATACAAACAACAATATAAACCCAA (SEQ ID NO: 11) | 5'FAM/ 3'BHQ1 |

The specificity of the TpG-specific PCR-system was demonstrated using test-templates (plasmid-DNA) as shown in Table No 2 as follows:

| Pipetted "TpG" plasmid [%] | Measured TpG [%] | Deviation |
|---|---|---|
| 100 | 100 | 0.00 |
| 99 | 99.07 | 0.07 |
| 97.5 | 97.9 | 0.41 |
| 95 | 95.27 | 0.28 |
| 90 | 89.1 | −1.00 |
| 75 | 71.11 | −5.19 |
| 50 | 51.09 | 2.18 |
| 25 | 28.6 | 14.40 |
| 10 | 12.81 | 28.10 |
| 5 | 5.92 | 18.40 |
| 2.5 | 2.76 | 10.40 |
| 1 | 0.36 | −64.00 |
| 0 | 0 | — |

For this, "TpG"-plasmids as designed were mixed with "CpG"-plasmids in order to simulate methylation values in a range between 100% and 0%. Then, the proportion (in %) of the TpG-template was determined in these mixtures using the inventive assay.

The cell type specificity (as measured by qPCR) was found as follows (table 3):

| Type of immune cell | qPCR-Detection [%] |
|---|---|
| CD8+ naive T-cells | 95.94 |
| CD8+ memory T-cells | 6.67 |
| all CTLs | 76.88 |
| T helper cells | 0.95 |
| B-cells | 0.15 |
| CD14+ monocytes | 0 |
| CD56 NK | 0 |
| CD56 NK T cells | 1.33 |
| CD15+ granulocytes | 0 |

The invention claimed is:

1. A method for producing an amplicon from a human endosialin (CD248) gene, the method comprising:
   a) bisulfite treating isolated genomic DNA from a human immune cell sample to generate bisulfite treated DNA, and
   b) amplifying a region of the CD248 gene from the bisulfite treated DNA to thereby produce the amplicon, wherein the amplifying is performed with a polymerase chain reaction (PCR) using methylation-specific primers that amplify a region of SEQ ID NO: 2 and the amplicon comprises thymine-guanine (TG) at nucleotide positions 274 and 275, 292 and 293, and 296 and 297 of SEQ ID NO: 2.

2. The method according to claim 1, further comprising detecting a methylation status of at least one cytosine-phosphate-guanine (CpG) position from the amplicon by a method selected from the group consisting of a methylation specific enzymatic digest, bisulfite sequencing, promoter methylation analysis, CpG island methylation analysis, MSP, HeavyMethyl, MethyLight, and Ms-SNuPE.

3. The method according to claim 1, wherein said human immune cell sample is obtained from a body fluid, a tissue, or an organ.

4. The method according to claim 1, wherein said method is performed without a step of purifying and/or enriching said sample.

5. The method according to claim 1, wherein said sample is derived from a human who suffers from or is likely to suffer from autoimmune diseases, transplant rejections, infection diseases, cancer, and/or allergy.

6. The method of claim 1, wherein the method is performed using a kit comprising:
a) a bisulfite reagent, and
b) materials for detecting a bisulfite convertible cytosine at CpG positions from the amplicon.

7. The method of claim 1, wherein the PCR uses an oligomer comprising the sequence of any of SEQ ID NOs: 4 to 13.

8. The method according to claim 1, wherein the amplicon comprises TG at nucleotide positions 274 and 275, 292 and 293, 296 and 297, and 319 and 320 of SEQ ID NO: 2.

9. The method according to claim 1, wherein said method is performed using whole blood and/or non-trypsinized tissue.

10. The method according to claim 1, wherein the amplicon comprises TG at nucleotide positions 274 and 275, 292 and 293, 296 and 297, 319 and 320, and 327 and 328 of SEQ ID NO: 2.

11. The method of claim 1, wherein the amplicon comprises SEQ ID NO: 2.

12. The method according to claim 1, wherein said human immune cell sample is obtained from a blood sample.

13. The method according to claim 1, wherein said human immune cell sample is a blood cell type.

14. The method according to claim 1, wherein said human immune cell sample comprises lymphocytes.

15. The method of claim 1, wherein the amplicon comprises TG at nucleotide positions 243 and 244, 274 and 275, 292 and 293, 296 and 297, 319 and 320 of SEQ ID NO: 2.

* * * * *

SEQUENCE LISTING

<160> NUMBER OF SEQ ID NOS: 13

<210> SEQ ID NO 1
<211> LENGTH: 439
<212> TYPE: DNA
<213> ORGANISM: Homo sapiens

<400> SEQUENCE: 1

```
catcttcctc atcctccccg tcatccagca actcatctcc gaggtcctgg gaagcctggg      60
cacccatggc ccctgcaggg ctgcagctga tgccatcagc ctccagctca tgtccctcgc     120
tacaataaca ctcgaagcca ccaacgtagt tgacacacat ctgctggcac acaccggcaa     180
tctggcactc atctgtgtcc acacagcggt gcggatcatc ctccgctggc cggaaaccca     240
ggcgacagtg gcagctgtag ccttgtggcc caccgggctc acactgctgc tcgcacggag     300
cctgggcaca ggggtcctcg caactgcgcc cgtctgctgc cagccggaag ccctcagtgc     360
agcggcagga cacgtgacca tccacctcct ccacacattc gtgttcgcag ccccgttgt     420 cagggctgca gccagtccc                                                   439
```

<210> SEQ ID NO 2
<211> LENGTH: 439
<212> TYPE: DNA
<213> ORGANISM: Homo sapiens

<400> SEQUENCE: 2

-continued

```
tatttttttt atttttttttg ttatttagta atttatttttt gaggttttgg gaagtttggg      60
tatttatggt ttttgtaggg ttgtagttga tgttattagt ttttagttta tgttttttgt       120
tataataata tttgaagtta ttaatgtagt tgatatatat ttgttggtat atattggtaa       180
tttggtattt atttgtgttt atatagtggt gtggattatt ttttgttggt tggaaatttta      240 ggtgatagtg gtagttgtag ttttgtggtt tattgggttt atattgttgt ttgtatggag       300
tttgggtata ggggttttttg taattgtgtt tgtttgttgt tagttggaag ttttttagtgt     360 agtggtagga tatgtgatta tttatttttt ttatatattt gtgtttgtag tttttgttgt       420
tagggttgta gttagtttt                                                    439
```

<210> SEQ ID NO 3
<211> LENGTH: 439
<212> TYPE: DNA
<213> ORGANISM: Homo sapiens

<400> SEQUENCE: 3

```
catcttcctc atcctccccg tcatccaaca actcatctcc gaaatcctaa aaaacctaaa       60
cacccataac ccctacaaaa ctacaactaa taccatcaac ctccaactca tatccctcgc      120
tacaataaca ctcgaaacca ccaacgtaat taacacacat ctactaacac acaccgacaa      180
tctaacactc atctatatcc acacaacgat acgaatcatc ctccgctaac cgaaaaccca      240
aacgacaata acaactataa ccttataacc caccgaactc acactactac tcgcacgaaa     300
cctaaacaca aaaatcctcg caactacgcc cgtctactac caaccgaaaa ccctcaatac     360
aacgacaaaa cacgtaacca tccacctcct ccacacattc gtattcgcaa ccccgttat     420 caaaactaca accaatccc                                                   439
```

<210> SEQ ID NO 4
<211> LENGTH: 18
<212> TYPE: DNA
<213> ORGANISM: Homo sapiens

<400> SEQUENCE: 4

```
catcttcctc atcctccc                                                     18
```

<210> SEQ ID NO 5
<211> LENGTH: 22
<212> TYPE: DNA
<213> ORGANISM: Homo sapiens

<400> SEQUENCE: 5

```
gggattggtt gtagttttga ta                                                22
```

<210> SEQ ID NO 6
<211> LENGTH: 22
<212> TYPE: DNA
<213> ORGANISM: Homo sapiens

<400> SEQUENCE: 6

```
ctatatccac acaacgatac ga                                                22
```

<210> SEQ ID NO 7
<211> LENGTH: 20
<212> TYPE: DNA
<213> ORGANISM: Homo sapiens

<400> SEQUENCE: 7
```

-continued

```
gttttcggtt ggtagtagac                                              20

<210> SEQ ID NO 8
<211> LENGTH: 21
<212> TYPE: DNA
<213> ORGANISM: Homo sapiens

<400> SEQUENCE: 8
aatcctcgca actacgcccg t                                            21

<210> SEQ ID NO 9
<211> LENGTH: 25
<212> TYPE: DNA
<213> ORGANISM: Homo sapiens

<400> SEQUENCE: 9
tatatagtgg tgtggattat ttttt                                        25

<210> SEQ ID NO 10
<211> LENGTH: 24
<212> TYPE: DNA
<213> ORGANISM: Homo sapiens

<400> SEQUENCE: 10
taacaacaaa caaacacaat taca                                         24

<210> SEQ ID NO 11
<211> LENGTH: 32
<212> TYPE: DNA
<213> ORGANISM: Homo sapiens

<400> SEQUENCE: 11
caaactccat acaaacaaca atataaaccc aa                                32

<210> SEQ ID NO 12
<211> LENGTH: 30
<212> TYPE: DNA
<213> ORGANISM: Homo sapiens

<400> SEQUENCE: 12
gtgtttatat agtggtgtgg attattmttt                                   30

<210> SEQ ID NO 13
<211> LENGTH: 25
<212> TYPE: DNA
<213> ORGANISM: Homo sapiens

<400> SEQUENCE: 13
ctaacaacaa acaaacacaa ttaca                                        25
```